(12) United States Patent
Kellner (10) Patent No.: US 8,672,971 B2
(45) Date of Patent: *Mar. 18, 2014

(54) CHIROPRACTIC TABLE APPARATUS AND METHOD OF USE

(76) Inventor: Bernwart Kellner, Keene, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/337,520

(22) Filed: Dec. 27, 2011

(65) Prior Publication Data

US 2012/0179203 A1    Jul. 12, 2012

Related U.S. Application Data

(63) Continuation of application No. 12/985,881, filed on Jan. 6, 2011, now Pat. No. 8,133,260.

(51) Int. Cl.
  *A61F 5/00* (2006.01)

(52) U.S. Cl.
  USPC .......................................... 606/241; 606/245

(58) Field of Classification Search
  USPC ........... 606/237, 240–245; 602/32, 33; 5/612, 5/613, 616–618; 128/845; 601/23, 24; 482/142
  See application file for complete search history.

(56) References Cited

U.S. PATENT DOCUMENTS

| | | | |
|---|---|---|---|
| 4,649,905 A | 3/1987 | Barnes | |
| 4,722,328 A | 2/1988 | Scott et al. | |
| 4,732,141 A * | 3/1988 | Steffensmeier | 606/245 |
| 6,638,299 B2 | 10/2003 | Cox | |
| 7,189,214 B1 | 3/2007 | Saunders | |
| 8,133,260 B1 * | 3/2012 | Kellner | 606/241 |

OTHER PUBLICATIONS

PCT International Search Report for PCT/US2012/020015 mailed Aug. 24, 2012.

* cited by examiner

*Primary Examiner* — Quang D Thanh
(74) *Attorney, Agent, or Firm* — Robert R. Deleault, Esq.; Mesmer & Deleault, PLLC (57) ABSTRACT

A chiropractic table has a base, a table support member connected to the base and extending upward from the base, an axial-lateral-tilt mechanism laterally connected to table support member, a cephalad section connected transversely to and being supported by the table support member above the base, a head section connected to and extending longitudinally from a first cephalad section end of the cephalad section, and a caudal section interconnected with the axial-lateral-tilt mechanism and the table support member and being positioned longitudinally adjacent a second cephalad section end of the cephalad section where the axial-lateral-tilt mechanism has an axial pivot mechanism configured to axially swing the caudal section along a predefined arc, the arc coinciding with a predefined radial distance from a pivot axis that is parallel to a longitudinal axis of the chiropractic table and located a predefined distance above a top surface of the chiropractic table.

16 Claims, 9 Drawing Sheets

CHIROPRACTIC TABLE APPARATUS AND METHOD OF USE

This application is a Continuation Application of Ser. No. 12/985,881, filed on Jan. 6, 2011, now U.S. Pat. No. 8,133,260 issued on Mar. 13, 2012.

BACKGROUND OF THE INVENTION

1. Field of the Invention

The present invention relates generally to chiropractic treatment tables. Particularly, the present invention related to chiropractic treatment tables of the type for generally horizontally supporting a patient in a face-down position.

2. Description of the Prior Art

The treatment of various maladies of the human body by means of the manipulation of the muscles and skeletal structure thereof, commonly referred to as "the practice of chiropractic", has become a widely used and accepted art. One such treatment regimen is to manipulate the muscles, ligaments and the osseous skeletal structures of the spine. The intervertebral disc is the strongest ligament of the spine. The architecture of a lumbar vertebra and the mechanics of a lumbar joint and the toughness of even a damaged disc do not allow for a lot of movement between adjacent vertebrae. Injury and degredation of the disc causes a breakdown of the disc and thus the deterioration of the intervertebral joint, which adversely affects the nervous system. A vertebral misalignment, the so called "subluxation," can only occur when the integrity of the disc has failed. Consequently, the optimal relationship between adjacent vertebrae gets interrupted and back pain, leg pain, muscle spasm and other signs and symptoms and abdominal problems appear. The same mechanisms apply and results manifest in the head, neck and upper torso, including shoulders, arms and hands, if there is injury to and deterioration of discs in the cervical spine and/or the thoracic spine.

Various chiropractic tables have been developed to facilitate this type of chiropractic and manual treatment. The conventional commercial table typically includes an elongated, padded platform or table on which a patient reclines. The table is further provided with means for securing the patient's extremities, e.g., the patient's ankles and a support of the arms. The conventional table is typically made up of two sections. One section is called the cephalad section, which is fixed, immovable and supported by rigid legs or support columns that rest on the floor. The other section is called the caudal section, which supports the patient's lower body. On the conventional chiropractic table the fixed or immobile cephalad section supports the patient's head and trunk including the pelvis The patient's legs are supported by the mobile or flexible caudal section. The table provides means for tiltably raising and lowering (extension and flexion, respectively), laterally bending, rotating and extending the lower body with respect to the upper body or the fixed support section. Such treatment tables have proven to be valuable aids to the practitioner of chiropractic medicine. Various treatment methods for patients suffering from spinal and related nerve, muscle, and skeletal maladies have been devised using such tables.

The mobile section is used to carry out flexiondistraction, also known as "decompression". The term "decompression" means that the nerve roots and/or the spinal cord are being decompressed. The distraction acts on the intervertebral discs since the vertebrae, being bone, resist decompression. "Flexion" is the bending of the spine at the lumbar level. Flexion is to the anterior (i.e., towards the floor). This should be associated by the patient with a comfortable and pleasant sensation of "stretching." Distraction is the separation of the cushions of the treatment table, and thus the spine, in the horizontal plane. In a few tables lateral bending is possible. This is also known as "lateral flexion." This movement by itself should also feel as a comfortable stretching sensation; but happens only if not too much force is applied. Fewer tables still have the option of "axial rotation." This means the mobile caudal section can swivel along the longitudinal axis of the table. In flexion, the whole disc is affected, though the emphasis is on the posterior part of the disc. In lateral bending the left side or the right side of the disc is being stretched. Stretching the disc has a stimulating and restorative effect on the disc. It helps the disc to regain its normal height and shape.

In flexiondistraction treatments, the patient is prone on the treatment table. Unphysiologic movement appears when flexiondistraction, lateral bending and axial rotation are combined, with time, the fourth dimension, in one action.

Therefore, what is needed is a device that facilitates the combined use of flexion and distraction, lateral bending and axial rotation so as not to introduce unphysiologic damaging forces into the lumbar spine during treatment.

SUMMARY OF THE INVENTION

There are problems associated with flexiondistraction type of treatments of the lumbar spine. If the spine were in contact with the cushions of the table, axial rotational decompression would take place in the lumbar spine. The patient's spine, however, is eight inches or more above the cushions while the cervical spine is about four inches or more above the cushions. When the cushions of an uncompensated table are axially rotated, unphysiologic shear forces come into play.

It is an object of the present invention to provide a device that facilitates the combined use of flexion and distraction, lateral bending and axial rotation that does not introduce unphysiologic forces into the lumbar spine during treatment.

The present invention achieves these and other objectives by providing a treatment table with a caudal section that supports the pelvis and the legs and provides for normal physiologic axial rotation/traction and lateral bending in combination or singly of the lumbar spine. In one embodiment, a chiropractic table has a base, a table support member, an axial-lateral-tilt mechanism, a cephalad section, a head section, and a caudal section. The table support member is connected to the base and extends upward from the base. The axial-lateral-tilt mechanism is laterally connected to the table support member. The cephalad section is connected transversely to and supported by the table support member above the base. The head section is connected to and extends longitudinally from a head end of the cephalad section. The caudal section is interconnected with the axial-lateral-tilt mechanism and the table support member and is positioned longitudinally adjacent the caudal end of the cephalad section. The axial-lateral-tilt mechanism has an axial pivot mechanism configured to axially pivot the caudal section through a predefined arc around a longitudinal pivot axis that is parallel to the longitudinal axis of the chiropractic table, the longitudinal pivot axis being located a predefined distance above a top surface of the chiropractic table.

In one embodiment of the axial pivot mechanism, the axial pivot mechanism has a tracking plate with an arcuate-shaped surface and a tracking rail with an arcuate-shaped surface where the tracking plate surface and the tracking rail surface are movably interconnected to provide movement of the caudal section through the predefined arc. The tracking plate is secured to one of a lower portion of the caudal section or an axial pivot support of the axial pivot mechanism and the tracking rail is connected to the other of the lower portion of the caudal section or the axial pivot support of the axial pivot mechanism.

In another embodiment of the axial pivot mechanism, the arcuate-shaped surface of the tracking plate and the arcuate-shaped tracking rail have a cross-sectional profile that interlocks the tracking plate to the tracking rail. One of the arcuate-shaped surface of the tracking plate or the arcuate-shaped surface of the tracking rail has a longitudinal channel and the other of the arcuate-shaped surface of the tracking plate or the arcuate-shaped surface of the tracking rail has a longitudinal ridge where the longitudinal channel and the longitudinal ridge are configured to mate to, cooperate with and operably engage each other.

In still another embodiment of the axial pivot mechanism, one of the arcuate-shaped surface of the tracking plate or the arcuate-shaped surface of the tracking rail has at least one rolling mechanism selected from the group consisting of a roller and a wheel where the at least one rolling mechanism is configured to roll on the arcuate-shaped surface of the other of the tracking plate or the tracking rail.

In a further embodiment of the present invention, the axial pivot mechanism further includes an axial pivot retaining mechanism fixedly attached to one of the tracking plate or the axial pivot support and configured to retain the tracking plate and the tracking rail in operable engagement to each other.

In yet another embodiment of the present invention, the predefined distance of the longitudinal pivot axis above a top surface of the chiropractic table is in a range of approximately eight to eighteen inches.

In another embodiment of the present invention, the predefined arc through which the caudal section rotates defines an arc angle of approximately fifty degrees.

In a further embodiment of the present invention, there is disclosed a method of providing normal physiologic axial rotation to a lumbar spine. The method includes providing a chiropractic table having a caudal section that supports the pelvis and the legs of a patient and providing an axial pivot mechanism connected to and supporting the caudal section. The axial pivot mechanism is adapted to axially pivot the caudal section through a predefined arc around a longitudinal pivot axis that is parallel to the longitudinal axis of the chiropractic table. The longitudinal pivot axis is located a predefined distance above a top surface of the chiropractic table depending on the thickness of the patient.

DETAILED DESCRIPTION OF THE PREFERRED EMBODIMENT

Figure 1:
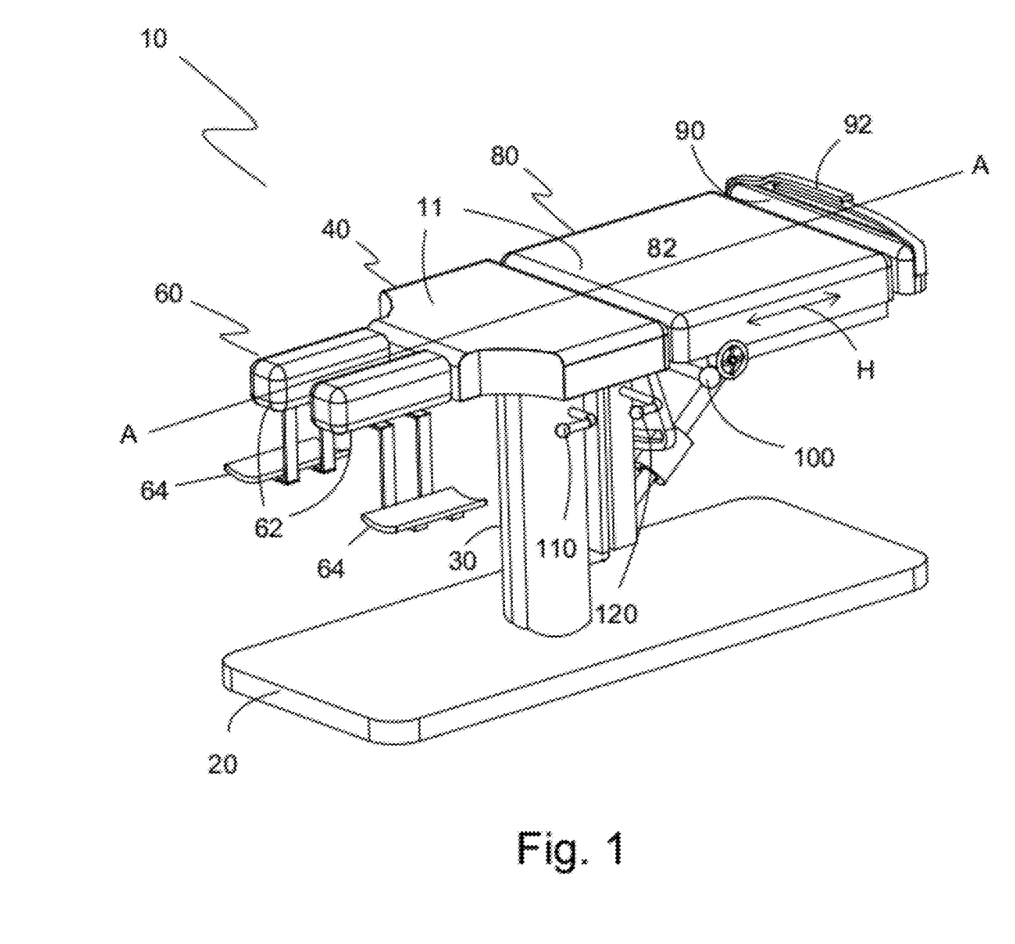
FIG. 1 is a perspective view of one embodiment of the present invention showing a chiropractic table.

The preferred embodiment(s) of the present invention is illustrated in FIGS. 1-8. FIG. 1 is a perspective view of one embodiment of a chiropractic table 10 according to the present invention for supporting a patient lying in a generally horizontal position face down on a top surface 11 for manually controllable chiropractic manipulation. The table 10 includes a base 20 and a table support member 30 on which is mounted a cephalad support section 40 for supporting the thorax of the patient. Table support member 30, which extends upward from base 20, is preferably a pedestal support but may also be a supporting framework, also supports a head support section 60 adjacent a head end of chiropractic table 10. It is contemplated that head section 60 has parallel cushions 62 that may optionally be adjusted toward or away from each other as well as arm rests 64, all of which is more clearly shown in FIGS. 2B and 3B. An opposite or foot end of chiropractic table 10 includes a caudal support section 80 also interconnected with, supported from and cantilevered to table support member 30.

Unlike conventional tables where the cephalad section supports the pelvis and the caudal section supports only the legs, the present invention defines the caudal section as that section of the table that supports the pelvis and the legs. This design allows full and free movement in all directions of the lumbar spine in accordance the newly gained insight of spinal motion under extension, flexion, lateral bending, lateral tilt and axial rotation. As long as the pelvis is on the cephalad section full therapeutic benefit is not possible and sheer within the lumbar spine will cause injury to an already compromised lumbar disc.

The caudal section 80 includes an ankle support cushion 90 and an optional ankle cuff 92 attached to the cushion for securing the ankles of a patient in place. For greater ease in the caudal manipulation of a patient on the table for treatment in flexion and/or distraction about a generally horizontal pitch axis extending transversely of the patient's spinal column across the hip region, the table may optionally be provided with a detachable assist bar (not shown) securable to support structure of caudal section 80 between the legs and near the ankles of the patient. A caudal support cushion 82 is movable and adjustable in a longitudinal direction along the central axis A-A of chiropractic table 10 as indicated by the arrow H to accommodate patients of different lengths. A counter pressure adjustable mechanism known to those of skill in the art is provided for controlling the amount of drop adjustment.

Each side of chiropractic table 10 is provided with a caudal lateral rotation lock lever 100, a caudal flexion lock lever 110 and a caudal pivotal lock lever 120. Duplication of each of these levers on an opposite side of the table provides for easy access and control of the chiropractic manipulation and treatment of a patient from either side of the table without the necessity of having to walk around the end of the table, merely to lock or unlock a particular component control lever. As illustrated, the respective levers 100, 110 and 120 each have control knobs adjacent the outer end and the levers are shown in a generally horizontal, locking position and are unlocked by downward movement of the outer end portions of the lever as indicated by the arrow J shown in FIG. 2A. Downward unlocking of the levers provides ease of operation for the chiropractor when treating and manipulating a patient.

Figure 2A:
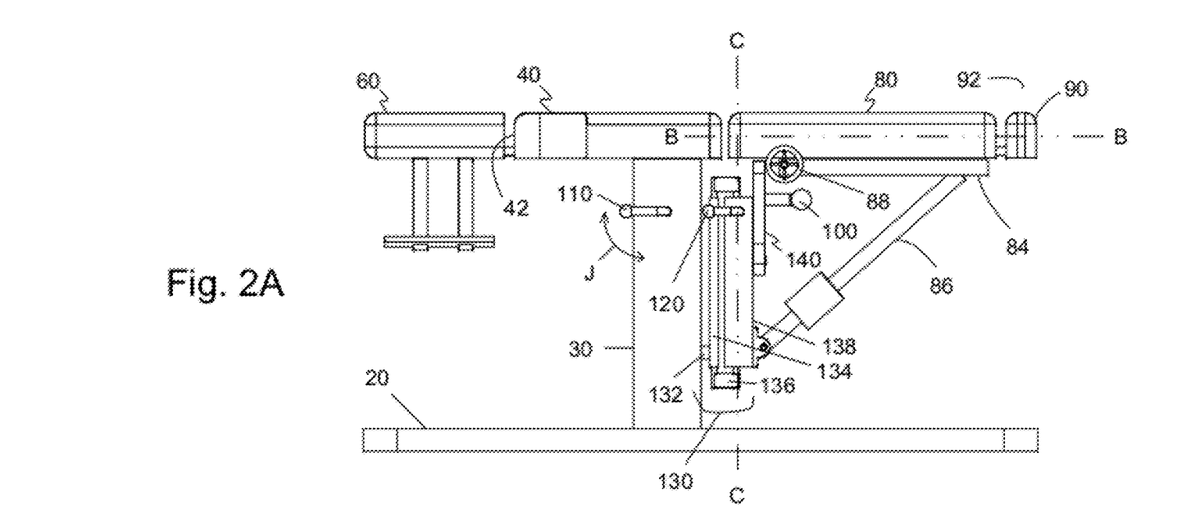
FIG. 2A is a side view of the chiropractic table in FIG. 1 showing the caudal section in a neutral position.
Figure 2B:
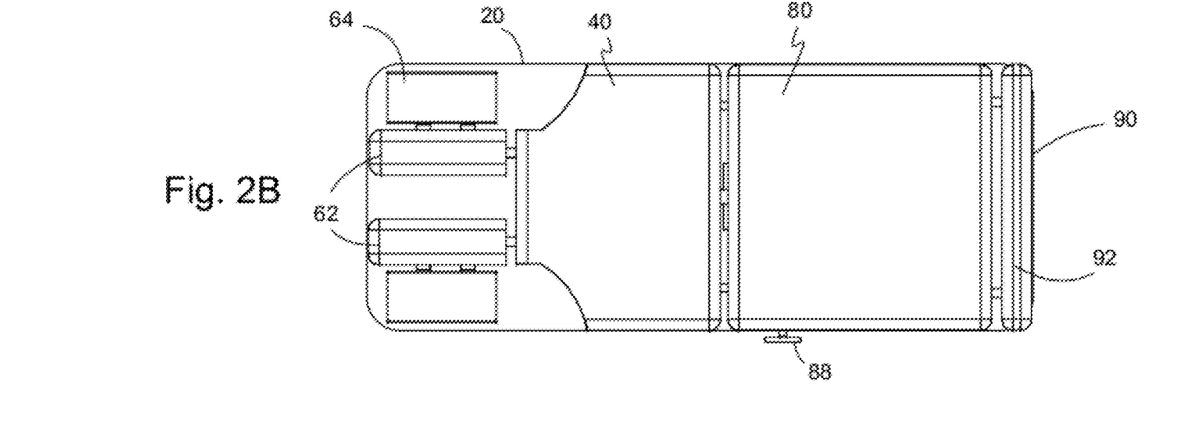
FIG. 2B is a top view of the chiropractic table in FIG. 2A.

Turning to FIG. 2A, 2B and in accordance with the present invention, caudal section 80 is interconnected and supported from the table support member 30 by an axial-lateral-tilt mechanism 130 that includes a tilt component 132, a lateral pivot support 134, a lateral pivot mechanism 136, an axial pivot support 138, and an axial pivot mechanism 140. Tilt component 132 is supported by table support member 30 on one end, is operably connected and controlled by caudal flexion lock lever 110, and supports lateral pivot support 134. Tilt component 132 may have several structural configurations such as, for example, a ball joint, U-joint, journal mechanism, pivot bar, and the like, which permits the caudal section to pivot downwardly in flexiondistraction about a generally horizontal, pitch axis extending laterally outwardly of a longitudinal axis of the table, all as is generally known by those of ordinary skill in the art. Lateral pivot mechanism 136 connects lateral pivot support 134 to axial pivot support 138 and permits axial pivot support 138 to pivot about an axis C that is transverse to the longitudinal axis B of caudal section 80 through a predefined arc shown in FIGS. 5A, 5B. Axial pivot support 138 connects to and supports axial pivot mechanism 140. Caudal section 80 further includes a rail assembly 84 that is connected on one end to axial pivot mechanism 140 and to a first end of a flexion actuator 86. Flexion actuator 86 is pivotally connected to pivot 138. It should be understood that head section 60 is connected to the head end 42 of cephalad section 40 and the ankle support cushion 90 to caudal section 80, using external or internal support framing that may optionally be adjustable with respect to a patient's height.

Figure 3A:
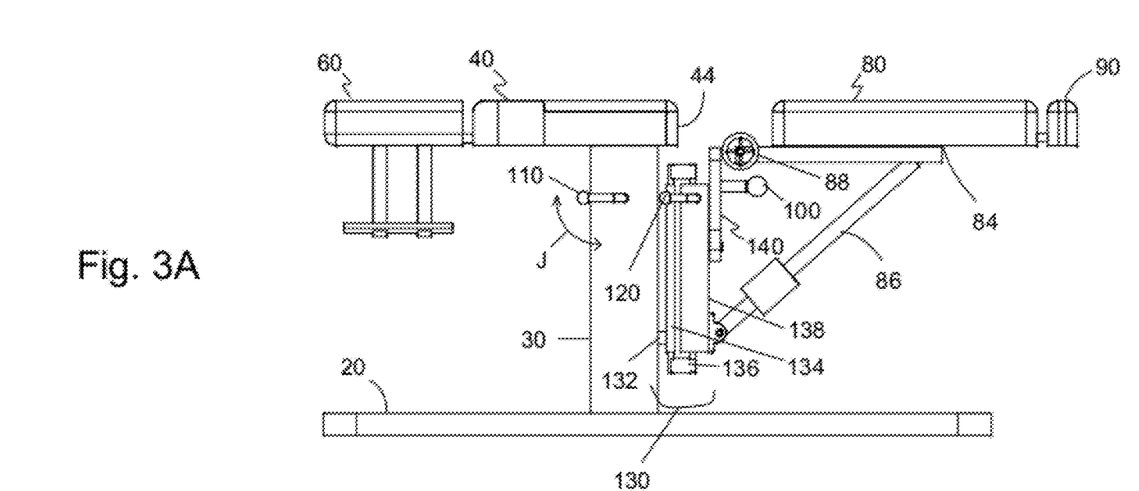
FIG. 3A is a side view of chiropractic table of FIG. 1 showing the caudal section in an extended/distracted position (not flexed).
Figure 3B:
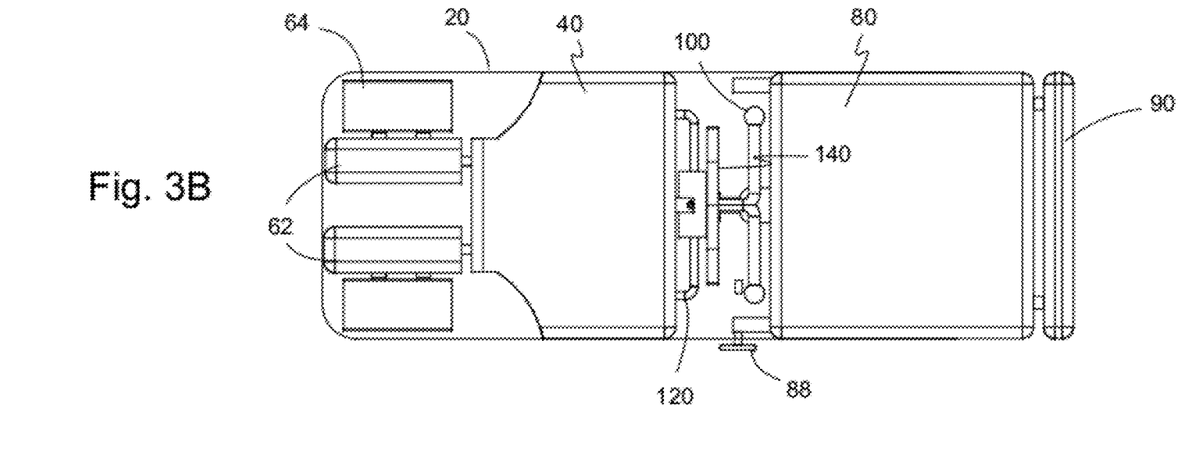
FIG. 3B is a top view of the chiropractic table in FIG. 3A.

Turning now to FIGS. 3A, 3B, there is illustrated chiropractic table 10 in an extended/distracted position. It is understood that the separation illustrated is exaggerated more clearly show that caudal section 80 is in an extended/distracted position and those of ordinary skill in the art will recognize that a patient's spine would not be able to undergo such a large distraction. In one embodiment, caudal cushion 82 is moved longitudinally away from the caudal end 44 of cephalad section 40 using a rail and gear mechanism (not shown) that is adjusted using adjusting wheel 88. This extension/distraction treatment is also, and more appropriately, called decompression since the spinal or peripheral nerve roots and the spinal cord are decompressed the pressure coming from the deformed intervertebral discs or the malpositioned vertebrae.

Figure 4A:
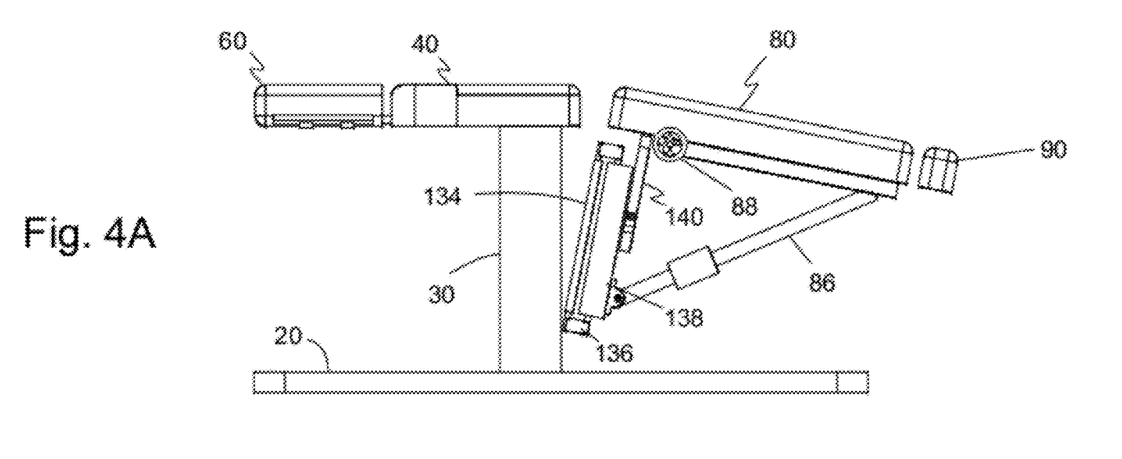
FIG. 4A is a side view of the chiropractic table of FIG. 1 showing the caudal section in flexion position.
Figure 4B:
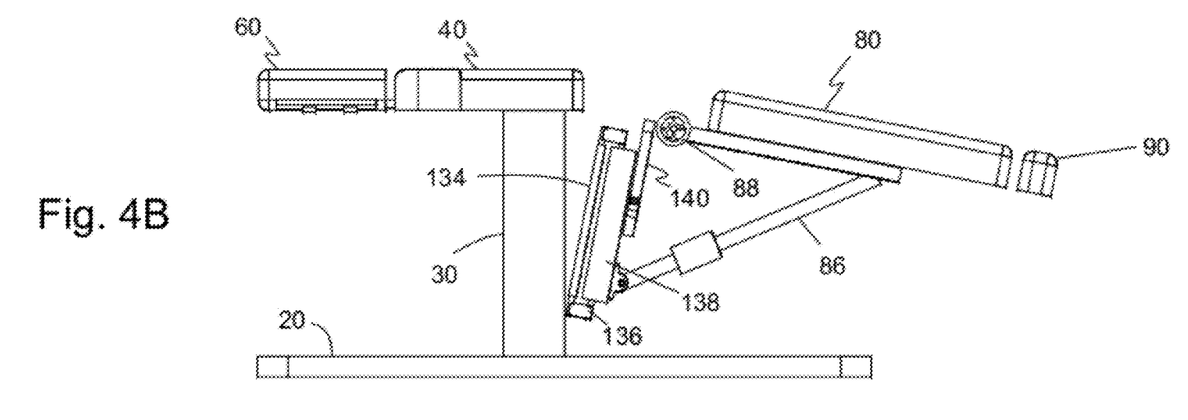
FIG. 4B is a side view of the chiropractic table in FIG. 4A showing the caudal section in an extended/distracted and flexion position.

Manipulation of caudal section 80 between a neutral position as shown in FIG. 2A and a lowered position as shown in FIG. 4A is known as flexiondistraction and is useful in the treatment of a patient. As illustrated in this embodiment in FIG. 4A, caudal section 80 is lowered toward base 20 by unlocking tilt component 132 (FIG. 2A) using caudal flexion lock lever 110 to disengage the lock that prevents tilt component 132 from pivoting and allowing caudal section 80 to move to the lower flexion position. FIG. 4B illustrates chiropractic table 10 in an extension and flexion distraction position. In an embodiment constructed in accordance with the present invention, pivotal movement in caudal flexion distraction from the level position to a lower position can be accommodated up to an amount of 20 degrees below the horizontal.

Figure 5A:
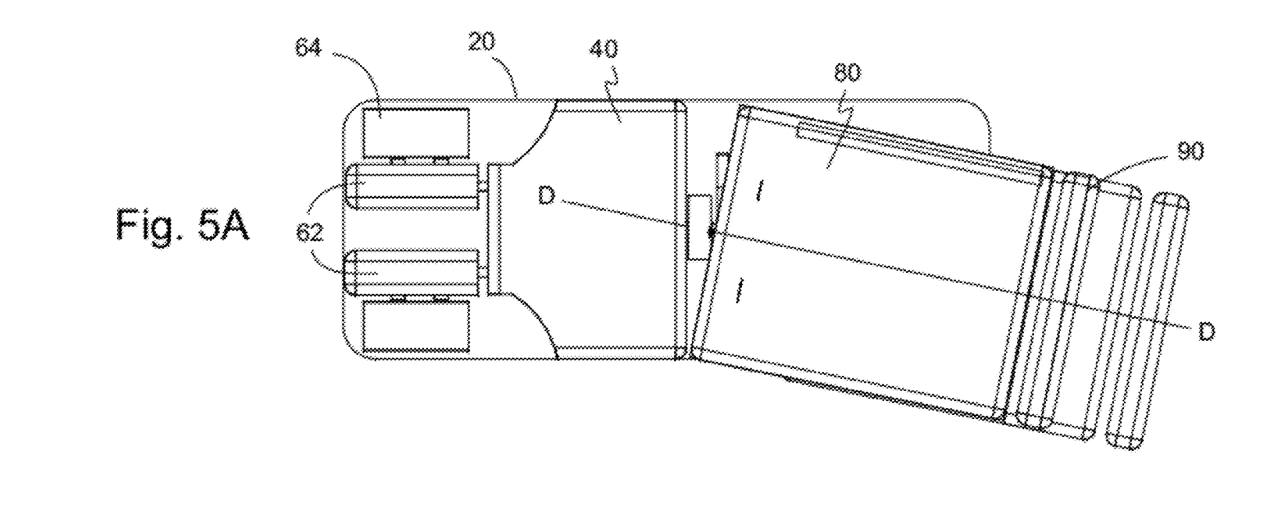
FIG. 5A is a top view of the chiropractic table in FIG. 1 showing the caudal section in an extended/distracted left flexion position.
Figure 5B:
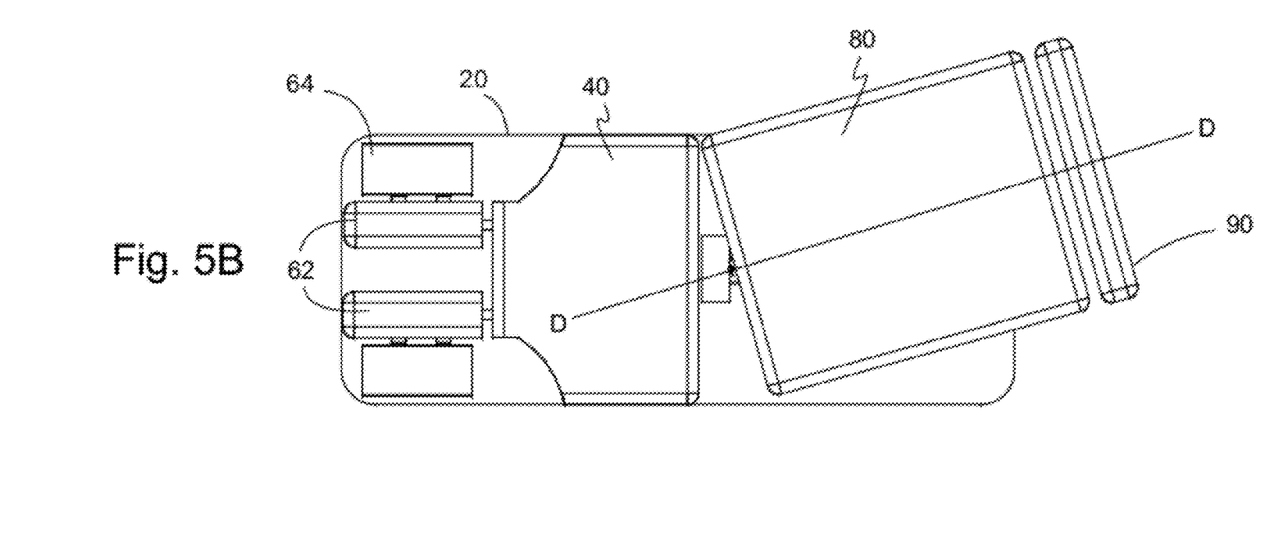
FIG. 5B is a top view of the chiropractic table in FIG. 1 showing the caudal section in an extended/distracted right flexion position.

Lateral pivotal swinging movement of the caudal section about a generally vertically extending yaw axis adjacent the cephadal support section 40 is termed caudal swinging action or lateral flexion. FIGS. 5A and 5B illustrate lateral flexion. In FIG. 5A, caudal section 80 is in a left lateral flexion position which also provides extension/distraction of the right side of the lumbar spine. To move caudal section 80 to this position, lateral rotation lock lever 100 is manipulated to unlock lateral pivot mechanism 136 and permits axial pivot support 138 to pivot about an axis C (FIG. 2A) that is transverse to the longitudinal axis B of caudal section 80 through a predefined arc. It is contemplated in another embodiment that lateral pivot mechanism 136 may also optionally permit lateral pivot support 134 to pivot in addition to axial pivot support 138. In FIG. 5B, caudal section 80 is in a right lateral flexion position which provides extension/distraction of the left side of the lumbar spine. By maintaining lateral rotation lock lever 100 in an unlocked position allows caudal section 80 to rotate through the predefined arc, which is typical for chiropractic tables that have the ability to provide lateral flexion. Lateral flexion or a swinging movement about the vertical yaw axis extending through the lateral pivot mechanism 136 can be accommodated up to 25 degrees right or left as indicated by the line D-D.

Figures 6A, 6B, 6C:
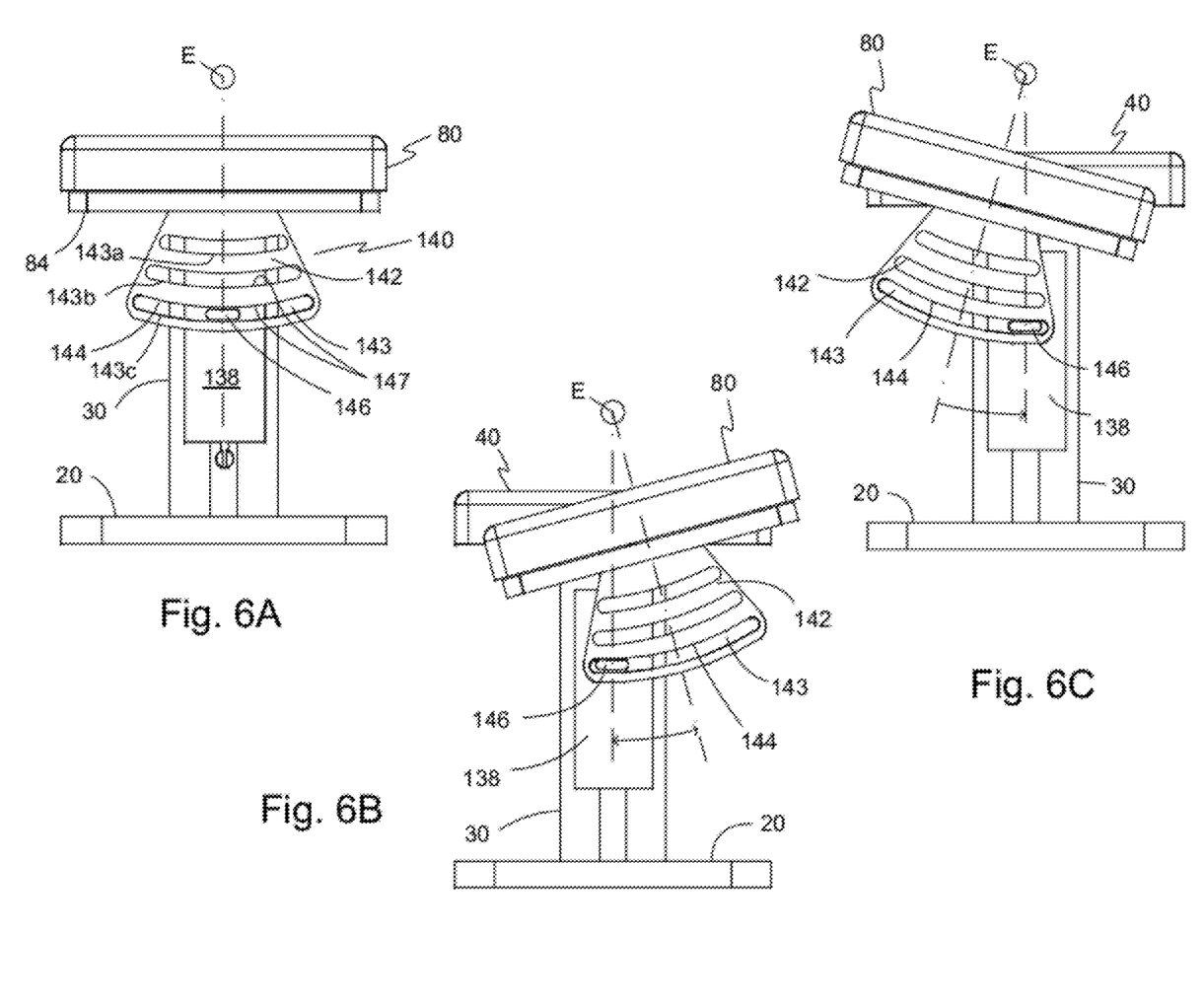
FIG. 6A is an end view of the chiropractic table in FIG. 1 taken from the ankle rest end showing the caudal section in a neutral axial position.
FIG. 6B is an end view of the chiropractic table in FIG. 1 taken from the ankle rest end showing the caudal section in a left axial flexion position.
FIG. 6C is an end view of the chiropractic table in FIG. 1 taken from the ankle rest end showing the caudal section in a right axial flexion position.

Turning now to FIG. 6A, there is illustrated an end view of chiropractic table 10 showing one embodiment of axial pivot support 138 and axial pivot mechanism 140 in a neutral position. In the preferred embodiment, axial pivot mechanism 140 includes a tracking plate 142 attached to caudal section 80 and a tracking rail or pin 146 attached to axial pivot support 138. The tracking rail or pin 146 may be repositioned to accommodate for the different arcs of the tracking plate on axial pivot support 138. A key feature of the axial pivot mechanism 140 is that the pivot point E of caudal section 80 is above the top of caudal section 80 and coincides with the spine of the patient when the patient is lying prone on the table (face down) This pivot point may be in a range of ten to eighteen inches or more above the top of caudal section 80 and varies from patient to patient, depending on the thickness of the patient. For example, the pivot point may have preset values such as ten, twelve, fourteen or sixteen inches or may be variably adjustable within the range described above. Typically, the thickness of the patient is measured from the front (abdomen) of the patient's abdomen to the spine while lying in prone position. When the thickness has been established, the practitioner then relocates or re-positions the tracking rail or pin 146 within the proper tracking rail 143. This position places the pivot point E at approximately the position of the lumbar spine so that rotation is effected about the center of the spine, which is the lumbar spine's axis of rotation. Locating the pivot point above the top of chiropractic table 10 prevents abnormal axial rotation of the lumbar spine. Abnormal axial rotation, which occurs when the rotating axis is located at either the longitudinal axis of caudal section 80 or at the top surface of chiropractic table 10, introduces sheer forces that are damaging to the disc, a disc that typically is already compromised when it needs treatment.

Tracking plate 142 has an arced groove or slot 143 whose radius is pre-determined based on the relative spatial position of the pivot point E (i.e. the spine) above chiropractic table 10.

Figure 8A:
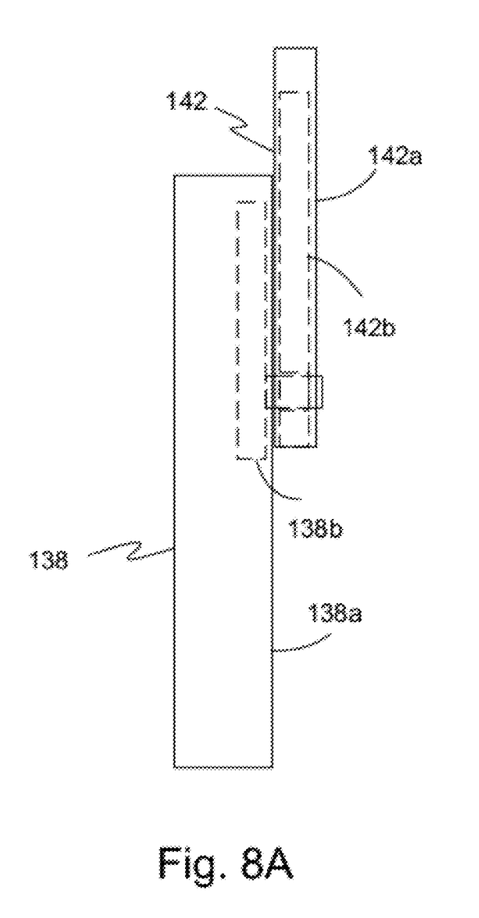
FIGS. 8A and 8B are cross-sectional views of the variable adjustable axial pivot support and the variable adjustable axial pivot mechanism.
Figure 8B:
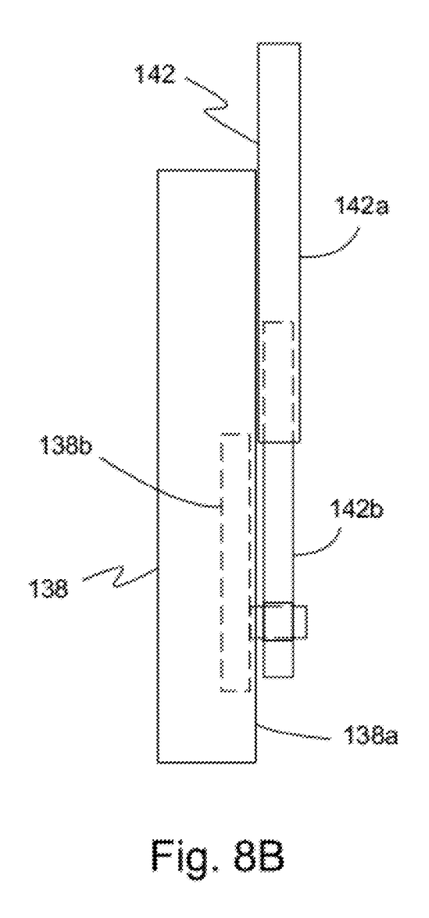

Optionally, plate 142 may have a plurality of arced grooves or slots 143a, 143b, 143c where the tracking rail or pin 146 may be re-positioned into one of the slots 143 that coincides with the thickness of the patient. Plate 142 may be constructed so that each slot 143 is located in plate 142 to provide for one inch or two inch incremental adjustments in patient thickness. For example, slot 143a may be located in plate 142 to coincide with a pivot point that is ten inches above the top surface of chiropractic table 10 while slots 143b and 143c may coincide with a pivot point that is twelve and fourteen inches above the chiropractic table 10, respectively. Alternatively, plate 142 may have a first and second plate portion 142a, 143b where first plate portion 142a is fixed to caudal section 80 and second plate portion 143b is adjustable along the longitudinal axis of first plate portion 142a of the plate 142 while being simultaneously adjustable along the longitudinal axis of axial pivot support 138, which has a first pivot support portion 138a and a second pivot support portion 138b, to provide a wider range of adjustment to accommodate a more variability in the thickness of each patient. This is more clearly and simply illustrated in FIGS. 8A and 8B. FIG. 8A illustrates the smallest patient thickness position and FIG. 8B illustrates the largest patient thickness position.

Figure 7A:
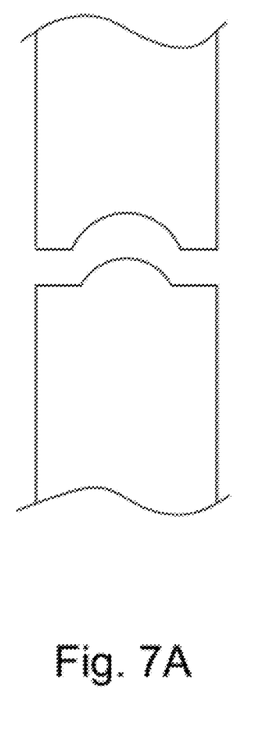
FIGS. 7A-7F are cross-sectional views of various embodiments of the profile of the arcuate-shaped surfaces of the tracking plate and the tracking rail of the present invention.
Figure 7B:
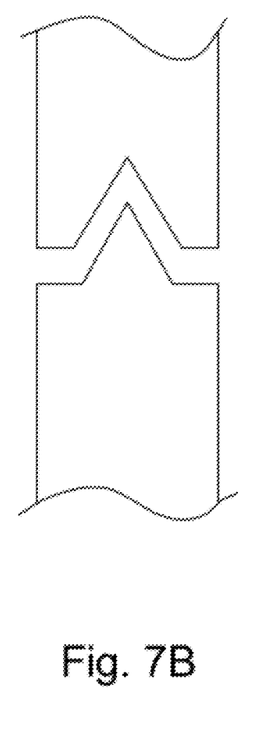
Figure 7C:
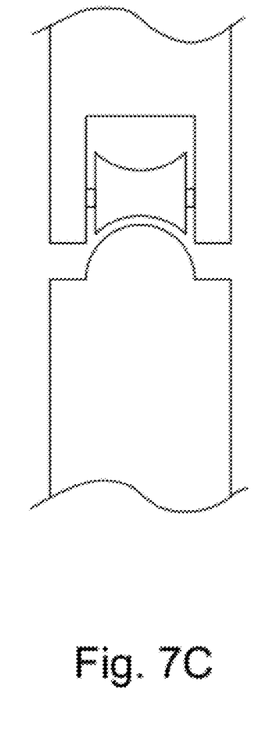
Figure 7D:
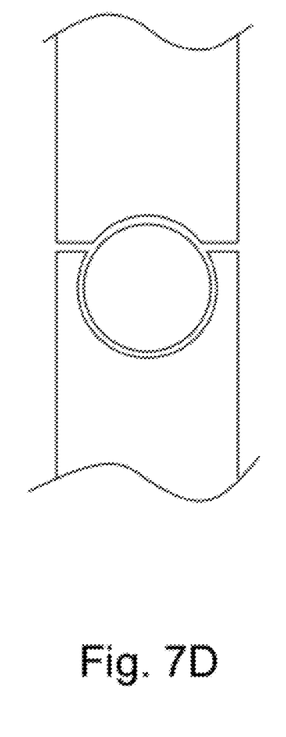
Figure 7E:
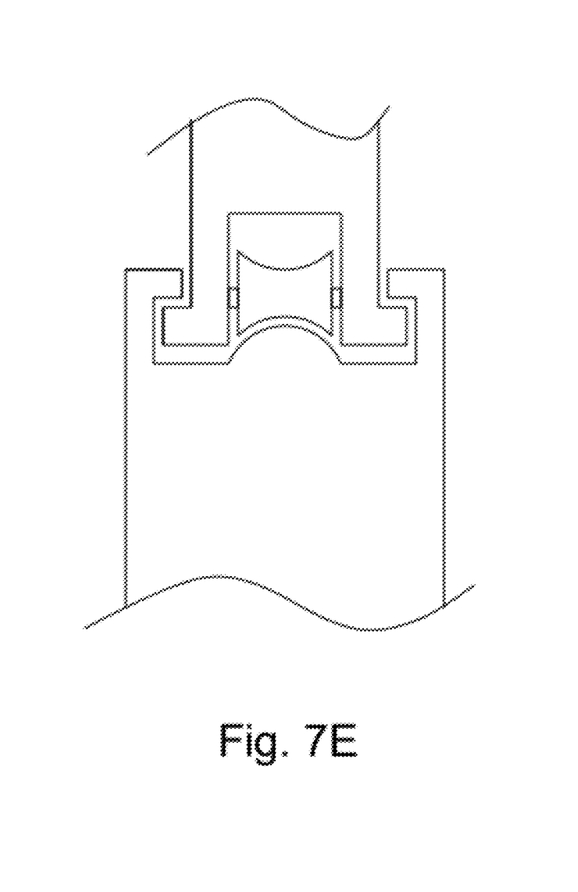
Figure 7F:
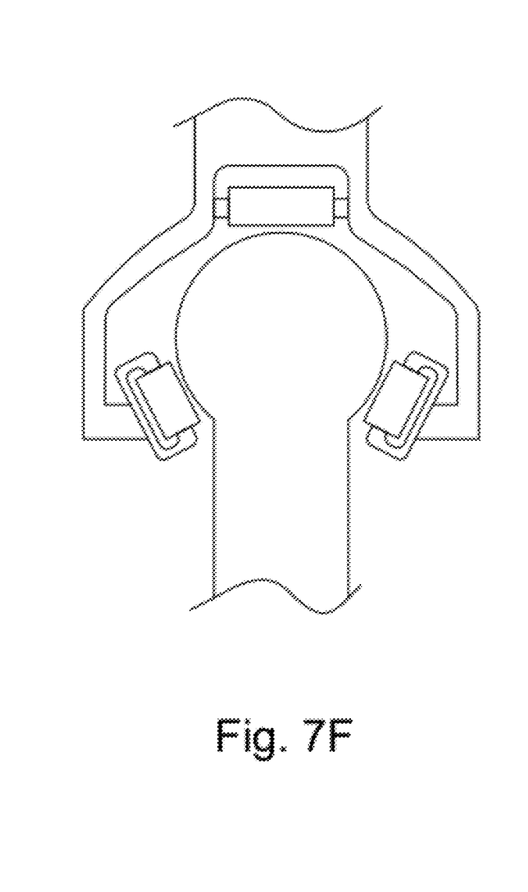

Arced groove or slot 143 may include low friction material along one or both sides 144 or other low friction structure such as, for example ball bearings or rollers. Tracking rail 146 is stationary and attached to axial pivot support 138. Tracking rail 146 preferably has an arced-shape that is substantially similar to the shape of arced groove or slot 143 and is positioned to slidably support tracking plate 142 and caudal section 80. Tracking rail 146 preferably has a low friction support surface 147 that contacts the corresponding support side 144 of arced groove or slot 143. The arcuate-shaped surface may be flat or contoured as illustrated in FIGS. 7A and 7B. It is contemplated that either arced groove/slot 143 or tracking rail 146 (or both) is configured to capture and slidably retain groove/slot 143 and tracking rail 146 to each other to prevent any inadvertent separation of tracking rail 146 from tracking groove/slot 143. Illustrated examples are shown in FIGS. 7E and 7F. It is further contemplated that tracking plate 142 may have only one or a set of tracking rollers or wheels (as illustrated in FIG. 7C) or ball bearings (as illustrated in FIG. 7D) or that capture the tracking rail much like the wheels or rollers of a modern amusement park ride that incorporates a rail or rails for supporting a moving cart. An illustrated example is shown in FIG. 7F. In summary, FIGS. 7A-7F are cross-sectional views illustrating some examples of tracking slot 143 and tracking rail 146.

In accordance with the present invention, caudal section 80 provides for caudal rotation of up to about 25 degrees in either direction from a horizontal position about a longitudinal pivot axis E-E spatially located above of the caudal section 80, which coincides with the spinal axis of the patient. FIGS. 6B and 6C illustrate the caudal rotation described. It is further contemplated that tracking slot 143 or the tracking rail 146 may be adjustable in the vertical direction to accommodate the "thickness" of a patient as previously explained. It is also contemplated that the tracking rail 146 may be connected to caudal section 80 while tracking plate 142 is connected to axial pivot support 138.

From the foregoing, it will be seen that the patient treatment table 10 provides an extremely useful design for wide ranging chiropractic manipulation including caudal flexion and/or distraction between the horizontal or neutral position and about 20 degrees down; lateral caudal flexion between about 25 degrees right or left of the center line; and axial caudal rotation of up to 25 degrees in either direction about a predefined longitudinal pivot axis E-E of the spinal cord axis.

In general, most treatment is accomplished with one or more levers in the locked position such as the caudal rotation lock lever 100 after a desired amount of caudal rotation is selected. The caudal flexiondistraction lock lever 110 and the caudal lateral lock lever 120 may be unlocked together for permitting simultaneous movement in caudal flexiondistraction in combination with caudal lateral action to the left or right. Moreover, for particular problems of patients, the caudal flexion lock lever 110 may be locked while manipulation is achieved only by caudal lateral movement and in converse, the caudal lateral lock lever 120 may be locked while caudal flexion or distraction is accomplished. Also, caudal axial rotation may be given to the left or the right side (down) where the other positions are in a locked state. Motorized versions of the above description are the optimal treatment options. Caudal manipulation may also be assisted by use of an optional detachable assist arm or handle (not shown) position between the caudal cushion 82 and foot section 90 in order to improve the chiropractor's working position in an upward or downward direction applied outwardly of tilt component 132. The detachable assist bar also provides better leverage for the chiropractor to swing the caudal section in lateral caudal flexion.

The advantage of the present invention is to provide a chiropractic table 10 that maintains natural alignment of lumbar spine in all planes during treatment. In the lumbar spine, discs suffer the greatest stresses and the greatest damage leading to premature disintegration. By using the mechanics described above, the treatment is directed to the deteriorating disc, the weakest segment. Treatment involves four movements on the treatment of low back disorders. The four movements include extension, flexion, lateral (left or right) flexion, and axial rotation. All of these movements can be done independently of one another or in any combination. The purpose is to treat the invertebral disc, also known as the invertebral ligament. The main components of this ligament are the nucleus pulposus and the annulus fibrosus. Breakdown of the annulus fibrosus is the reason for degenerative disc disease, disc bulge, disc protrusion, disc prolapsed, annular tear, radial tear and loss of disc height. Some secondary symptoms are obscure back pain, muscular back pain, muscle spasms, sciatica and other leg pain, burning, numbness and tingling in legs and/or feet, organ dysfunction and/or failure in the abdomen and pain in the attachment of muscles and tendons where they attach on a bone. All of these conditions can be totally debilitating. Disease and symptoms of "mechanical" origin are not treatable successfully with medications. Physiological means, for example, flexiondistraction and decompression in combination with other positions, are very effective in the treatment of disc-related disorders. Unlike prior art tables, the caudal section as defined above includes support for the pelvis and legs and provides for axial rotation of the lumbar vertebrae and discs while maintaining natural physiological relationships. In prior art tables where the pelvis is on the cephalad section, full therapeutic benefit is not possible. Sheer results, which will cause injury to the already compromised lumbar discs and spine.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A chiropractic table comprising:
a base;
a table support member connected to the base and extending upward from the base;
an axial-lateral-tilt-flexion mechanism laterally connected to the table support member;
a cephalad section connected transversely to and being supported by the table support member above the base;
a head section connected to and extending longitudinally from a head end of the cephalad section; and
a caudal section interconnected with the axial-lateral-tilt-flexion mechanism and the table support member wherein the axial-lateral-tilt-flexion mechanism enables the caudal section to provide axial, lateral and tilt flexion, the caudal section being positioned longitudinally adjacent a caudal end of the cephalad section wherein the axial-lateral-tilt-flexion mechanism has an axial pivot mechanism configured to axially rotate the caudal section about an axis of rotation parallel to a longitudinal axis of the caudal section where the axis of rotation is positioned a predefined distance above a top surface of the caudal section.

2. The chiropractic table of claim 1 wherein the axial pivot mechanism has a tracking plate selected from the group consisting of:
(i) a tracking plate having an arcuate-shaped tracking plate surface and a tracking rail being movably interconnected to provide movement of the caudal section along an arc defined by rotation of the caudal section about the axis of rotation,
(ii) a tracking plate having an arcuate-shaped tracking plate surface and a tracking rail each having a cross-sectional profile that interlocks the tracking plate to the tracking rail,
(iii) a tracking plate having an arcuate-shaped tracking plate surface and a tracking rail, wherein one of the arcuate-shaped tracking plate surface or the tracking rail has a longitudinal channel, and the other of the arcuate-shaped tracking plate surface or the tracking rail has a longitudinal ridge, wherein the longitudinal channel and the longitudinal ridge are configured to mate to and operably engage with each other, and
(iv) a tracking plate having an arcuate-shaped tracking plate surface and a tracking rail, wherein one of the arcuate-shaped tracking plate surface or a tracking rail has at least one rolling mechanism selected from the group consisting of a roller and a wheel, wherein the at least one rolling mechanism is configured to roll on the other of the arcuate-shaped tracking plate surface or the tracking rail.

3. The chiropractic table of claim 2 wherein the tracking plate is secured to one of a lower portion of the caudal section or an axial pivot support of the axial pivot mechanism and the tracking rail is connected to the other of the lower portion of the caudal section or the axial pivot support of the axial pivot mechanism.

4. The chiropractic table of claim 2 wherein the axial pivot mechanism further includes an axial pivot retaining mechanism fixedly attached to one of the tracking plate or an axial pivot support and configured to retain the tracking plate and the tracking rail in operable engagement to each other.

5. The chiropractic table of claim 1 wherein the axis of rotation is in a range of about eight inches to eighteen inches from the top surface of the caudal section.

6. The chiropractic table of claim 1 wherein the caudal section rotates about the axis of rotation in a predefined arc that defines an internal angle from a neutral position of approximately twenty-five degrees in each direction.

7. A method of providing normal physiologic axial rotation to a lumbar spine, the method comprising:
providing a chiropractic table having a caudal section adapted to support a pelvis and legs of a patient;
providing an axial-lateral-tilt-flexion mechanism interconnected to the caudal section that enables the caudal section to provide axial, lateral and tilt flexion of the lumbar spine, wherein the axial-lateral-tilt-flexion mechanism including an axial pivot mechanism; and
providing the axial pivot mechanism connected to and supporting the caudal section wherein the axial pivot mechanism is adapted to rotate the caudal section about an axis of rotation parallel to a longitudinal axis of the caudal section where the axis of rotation is positioned at a predefined distance above a top surface of the caudal section.

8. The method of claim 7 wherein the step of providing the axial pivot mechanism further includes locating the predefined distance of the axis of rotation in a range of about eight inches to about eighteen inches from the top surface of the chiropractic table.

9. The method of claim 7 wherein the step of providing the axial pivot mechanism further includes defining an arc of fifty degrees along which the caudal section is rotated.

10. The method of claim 7 wherein the step of providing the axial pivot mechanism further includes forming a tracking plate with an arcuate-shaped surface and a tracking rail with an arcuate-shaped surface selected from the group consisting of
(i) forming the arcuate-shaped surface of the tracking plate and the arcuate-shaped surface of the tracking rail to be movably interconnected to rotate the caudal section about the axis of rotation,
(ii) forming a cross-sectional profile of the arcuate-shaped surface of the tracking plate and the arcuate-shaped surface of the tracking rail to interlock the tracking plate to the tracking rail, and
(iii) forming a longitudinal channel into one of the arcuate-shaped surface of the tracking plate or the arcuate-shaped surface of the tracking rail and forming a longitudinal ridge into the other of the arcuate-shaped surface of the tracking plate or the arcuate-shaped surface of the tracking rail, wherein the longitudinal channel and the longitudinal ridge are configured to mate to each other.

11. The method of claim 10 wherein forming the tracking plate and the tracking rail includes securing one of the tracking plate or the tracking rail to a lower portion of the caudal section and securing the other of the tracking plate or the tracking rail to an axial pivot support of the axial pivot mechanism.

12. The method of claim 10 wherein forming the tracking plate and the tracking rail includes disposing at least one rolling mechanism selected from the group consisting of a roller and a wheel within the longitudinal channel and configuring the rolling mechanism to roll on the longitudinal ridge.

13. The method of claim 10 further comprising forming an axial pivot retaining mechanism and fixedly attaching the axial pivot retaining mechanism to one of the tracking plate or an axial pivot support and configuring the axial pivot retaining mechanism to hold the tracking plate and the tracking rail in operable engagement to each other.

14. The method of claim 7, further comprising the step of adjusting the axial pivot mechanism, wherein the axis of rotation coincides with a patient's lumbar spine axis.

15. A chiropractic table apparatus to provide axial rotation to a lumbar spine of a patient, the apparatus comprising:
- a caudal section adapted to support the patient's lumbar spine;
- an axial-lateral-tilt-flexion mechanism interconnected to the caudal section that enables the caudal section to provide axial, lateral and tilt flexion of the lumbar spine, wherein the axial-lateral-tilt-flexion mechanism including an axial pivot mechanism; and
- wherein the axial pivot mechanism is attached to the caudal section of the chiropractic table and adapted to rotate the caudal section of a chiropractic table about an axis of rotation parallel to a longitudinal axis of the caudal section where the axis of rotation is positioned at a predefined distance above a top surface of the caudal section.

16. The apparatus of claim 15 wherein the axial pivot mechanism is located below the caudal section and has a tracking plate with an arcuate-shaped tracking plate surface and a tracking rail selected from the group consisting of
- (i) the arcuate-shaped tracking plate surface of the tracking plate and the tracking rail being movably interconnected to provide movement of the caudal section through a predefined arc,
- (ii) the arcuate-shaped tracking plate surface of the tracking plate and the tracking rail have a cross-sectional profile that interlocks the tracking plate to the tracking rail,
- (iii) one of the arcuate-shaped tracking plate surface of the tracking plate or the tracking rail has a longitudinal channel and the other of the arcuate-shaped tracking plate surface of the tracking plate or the tracking rail has a longitudinal ridge, wherein the longitudinal channel and the longitudinal ridge are configured to mate to and operably engage each other, and
- (iv) one of the arcuate-shaped tracking plate surface of the tracking plate or the tracking rail has at least one rolling mechanism selected from the group consisting of a roller and a wheel, wherein the at least one rolling mechanism is configured to roll on the other of the arcuate-shaped tracking plate surface of the tracking plate or the tracking rail.

* * * * *